(12) United States Patent
Parkhouse

(10) Patent No.: US 7,003,353 B1
(45) Date of Patent: Feb. 21, 2006

(54) PHOTOVOLTAIC POWERED CHARGING APPARATUS FOR IMPLANTED RECHARGEABLE BATTERIES

(75) Inventor: Leon Parkhouse, Los Angeles, CA (US)

(73) Assignee: Quallion LLC, Sylmar, CA (US)

( * ) Notice: Subject to any disclaimer, the term of this patent is extended or adjusted under 35 U.S.C. 154(b) by 303 days.

(21) Appl. No.: 10/676,203

(22) Filed: Sep. 30, 2003

Related U.S. Application Data

(60) Provisional application No. 60/432,116, filed on Dec. 10, 2002.

(51) Int. Cl.
*A61N 1/08* (2006.01)

(52) U.S. Cl. .................... 607/45; 607/61; 320/108
(58) Field of Classification Search ............. 607/61, 607/45; 320/108
See application file for complete search history.

(56) References Cited

U.S. PATENT DOCUMENTS

| | | | |
|---|---|---|---|
| 3,844,840 A | 10/1974 | Bender | 136/251 |
| 4,379,988 A | 4/1983 | Mattatall | 320/108 |
| 4,551,857 A | 11/1985 | Galvin | 2/7 |
| 4,665,896 A | 5/1987 | LaForge et al. | 623/3.1 |
| 4,748,344 A | 5/1988 | Sing | 307/150 |
| 4,827,534 A | 5/1989 | Haugen | 2/108 |
| 5,199,429 A | 4/1993 | Kroll et al. | 607/5 |
| 5,210,804 A | 5/1993 | Schmid | 381/323 |
| 5,211,321 A | 5/1993 | Rodriguez | 224/604 |
| 5,253,300 A | 10/1993 | Knapp | 381/323 |
| 5,303,305 A | 4/1994 | Raimo et al. | 381/323 |
| 5,610,494 A | 3/1997 | Grosfilley | 320/113 |
| 5,610,496 A | 3/1997 | Hofbauer et al. | 320/127 |
| 5,695,885 A | 12/1997 | Malhi | 429/7 |
| 5,831,198 A | 11/1998 | Turley et al. | 89/1.11 |
| 5,929,597 A | 7/1999 | Pfeifer et al. | 320/107 |

(Continued)

FOREIGN PATENT DOCUMENTS

| | | |
|---|---|---|
| EP | 0 515 059 B2 | 12/2000 |

(Continued)

OTHER PUBLICATIONS

Kazuya Goto et al., An Implantable Power Supply with an Optically Rechargeable Lithium Battery, IEEE Transactions on Biomedical Engineering, vol. 48, No. 7, Jul. 2001.

(Continued)

*Primary Examiner*—Robert E. Pezzuto
*Assistant Examiner*—Joy Patel
(74) *Attorney, Agent, or Firm*—Gavrilovich, Dodd & Lindsey, LLP

(57) ABSTRACT

A photovoltaic powered charging unit is mounted in a head covering, such as a cap or hat, for a patient who has an inductively chargeable medical device implanted in his head. The implanted device includes an implanted battery which powers the device. The photovoltaic cells provide continuous charging for the implanted battery and power for the implanted device when subjected to light. The charging unit includes a nonphotovoltaic cell that may be used to charge the implanted battery and power the implanted device in the absence of sufficient power from the photovoltaic cells. The cap has a sending coil located so that when the wearer dons the cap, the sending coil aligns with a receiving coil implanted in the patient's skull or brain. The implanted receiving coil is coupled to provide charging current to the implanted battery and power to the implanted device.

23 Claims, 11 Drawing Sheets

U.S. PATENT DOCUMENTS

| | | | |
|---|---|---|---|
| 5,996,115 A | 12/1999 | Mazelsky | 2/2.5 |
| 6,091,015 A | 7/2000 | Del Valle et al. | 136/243 |
| 6,106,971 A | 8/2000 | Spotnitz | 429/98 |
| 6,265,100 B1 | 7/2001 | Saaski et al. | 429/163 |
| 6,275,681 B1 | 8/2001 | Vega et al. | 455/41.1 |
| 6,310,960 B1 | 10/2001 | Saaski et al. | 381/323 |
| 6,366,056 B1 | 4/2002 | Podrazhansky et al. | 320/141 |
| 6,388,422 B1 | 5/2002 | Lew | 320/107 |
| 6,429,621 B1 | 8/2002 | Arai | 320/101 |
| 6,462,513 B1 | 10/2002 | Bradus et al. | 320/125 |
| 6,476,581 B1 | 11/2002 | Lew | 320/107 |
| 6,586,906 B1 | 7/2003 | Bessa et al. | 320/101 |
| 2002/0004167 A1 | 1/2002 | Jenson et al. | 429/162 |
| 2002/0084767 A1 | 7/2002 | Arai | 320/101 |
| 2005/0004619 A1 * | 1/2005 | Wahlstrand et al. | 607/45 |

FOREIGN PATENT DOCUMENTS

| | | |
|---|---|---|
| GB | 2 347 339 A | 9/2000 |
| GB | 2 370 509 A | 7/2002 |
| JP | 6173109 A2 | 6/1994 |
| JP | 8126460 A2 | 5/1996 |
| JP | 9157934 A2 | 6/1997 |
| JP | 2001069686 A2 | 3/2001 |
| WO | WO 94/00888 | 1/1994 |
| WO | WO 00/38216 | 6/2000 |

OTHER PUBLICATIONS

Photon 128, obtained from the Solar Rechargeable Hearing Aid website, [retrieved on Dec. 9, 2003] retrieved from the internet at , <http://www.ibis.bw/-mwb/solaraid.html>.

Photon 128-Brochure, obtained from the Solar Rechargeable Hearing Aid website, [retrieved on Dec. 9, 2003] retrieved from the Internet at , <http://www.ibis.bw/-mwb/brochure.html >.

Solar Powered Hearing Aids for Unreached People, obtained from the ComCare International website, [retrieved on Dec. 9, 2003] retrieved from the internet at , <http://www.comcareInternational.org/hearing.html>.

ComCare Model GLW: A Hearing Aid for Developing Countries, obtained from the ComCare International website, [retrieved on Dec. 9, 2003] retrieved from the internet at, <http://_comcareinternational.org/hearing_glw.html>.

* cited by examiner

PHOTOVOLTAIC POWERED CHARGING APPARATUS FOR IMPLANTED RECHARGEABLE BATTERIES

REFERENCE TO PRIOR FILED APPLICATIONS

This application claims the benefit of U.S. Provisional Application 60/432,116 filed Dec. 10, 2002.

FIELD OF THE INVENTION

This invention relates to a rechargeable battery and more particularly to apparatus for recharging an implanted rechargeable battery.

BACKGROUND OF THE INVENTION

Implantable medical devices such as speech processors and neurostimulators are typically battery-powered. Although battery technology for such devices continues to deliver ever-longer cell lifetimes, eventually the battery or batteries in an implantable device must be replaced or recharged. Because replacement requires surgical extraction of an implanted medical device, the use of rechargeable ("secondary") batteries is increasingly favored. The battery of an implanted medical device can be recharged transcutaneously, with the device in situ and a battery charger positioned outside of tissue. Inductive charging units are used to recharge implanted batteries. Inductively recharging an implanted device's battery through the skin requires a patient to properly align a charger with respect to the device's recharging circuitry, and keep it there during the recharging period. One such inductance charging unit has a sending (primary) coil powered by a rechargeable cell and incorporates a metal detector to aid in location of a receiving (secondary) coil in an implanted device. The recharging is done daily, and can take up to an hour at a time. This procedure can be inconvenient, uncomfortable, and a source of anxiety for the patient, and requires him to remember to recharge the battery.

SUMMARY OF THE INVENTION

Therefore, one object of the invention is to provide comfortable charging of the rechargeable power source of an implanted medical device, by means of an inductive charger, without requiring the patient to monitor the position of the sending coil in relation to the implanted receiving coil. The rechargeable power source in the implanted device may comprise one or more cells, a capacitor, or a hybrid of the two; for convenience, the word "battery" as used herein may refer to any or all of these.

Another object of the invention is to provide means to prolong the life of the implanted battery.

Another object of the invention is to increase the amount of time between required rechargings.

A battery charger is therefore provided having features selected to meet the above and other objects. The invention includes a photovoltaic powered inductive charging unit mounted to a head covering, such as a cap or hat, for a patient who has an inductively-chargeable device implanted in the skull or brain. Photovoltaic cells provide continuous charging and power for the implanted device when light impinges on the photovoltaic cells. Simply exposing the cap to a natural or artificial light source while wearing it during a portion of each day is sufficient to charge and power the implanted device.

The battery charger may incorporate a conventional baseball cap. The cap has a sending coil located so that, when the wearer dons the cap, the sending coil lines up with the receiving coil of the implanted device in the patient's skull or brain. A plurality of photovoltaic cells are disposed around the crown of the cap, in order to cover maximum space to maximize efficiency while still maintaining the shape and aesthetics of the baseball cap.

The battery charger includes a nonphotovoltaic cell, such as a rechargeable battery, which may also be charged by the photovoltaic cells. The nonphotovoltaic cell may be used to charge the implanted device in the absence of sufficient power from the photovoltaic cells. Alternatively, the nonophotovoltaic cell may be a non-rechargeable ("primary") battery. In that case, the primary battery would need to be replaced periodically to ensure sufficient charge.

The battery charger includes a charge controller to control the source and magnitude of a charging current provided to the sending coil. The charge controller is mounted at the edge of the cap, preferably in proximity to the sending coil. The photovoltaic cells are electrically connected to the charge controller. The nonphotovoltaic cell is also electrically connected to the charge controller and mounted in the front portion of the cap, preferably on the junction between the crown and the visor. By investing the battery charger with the ability to power the implanted device by the sending coil, the life of the implanted rechargeable battery may be prolonged by reducing the number of charging cycles.

LED's are mounted on the underside of the visor, remaining just in the peripheral field of normal view, to indicate diagnostic information about the implanted battery. Such information may include whether the battery is in a fully charged state, is being charged, or is completely discharged, which may be indicated by green, yellow, and red, respectively. The LEDs are of a low profile design for easy viewing by the wearer.

The implanted device includes a rechargeable battery, a battery management system, and a receiving coil.

The battery management system and charge controller operate cooperatively to direct power to the implanted device by way of the implanted rechargeable battery, the battery in the cap, or the photovoltaic cells on the cap. The charge controller on the cap has the ability to charge the battery from either an external source (AC or DC), or from the photovoltaic cells. The battery management system in the implanted device can provide power from the receiving coil to operate the implanted device while the implanted battery is being charged by the receiving coil.

DETAILED DESCRIPTION

The following text describes a preferred mode presently contemplated for carrying out the invention and is not intended to describe all possible modifications and variations consistent with the spirit and purpose of the invention. The scope of the invention should be determined with reference to the claims.

Figure 1:
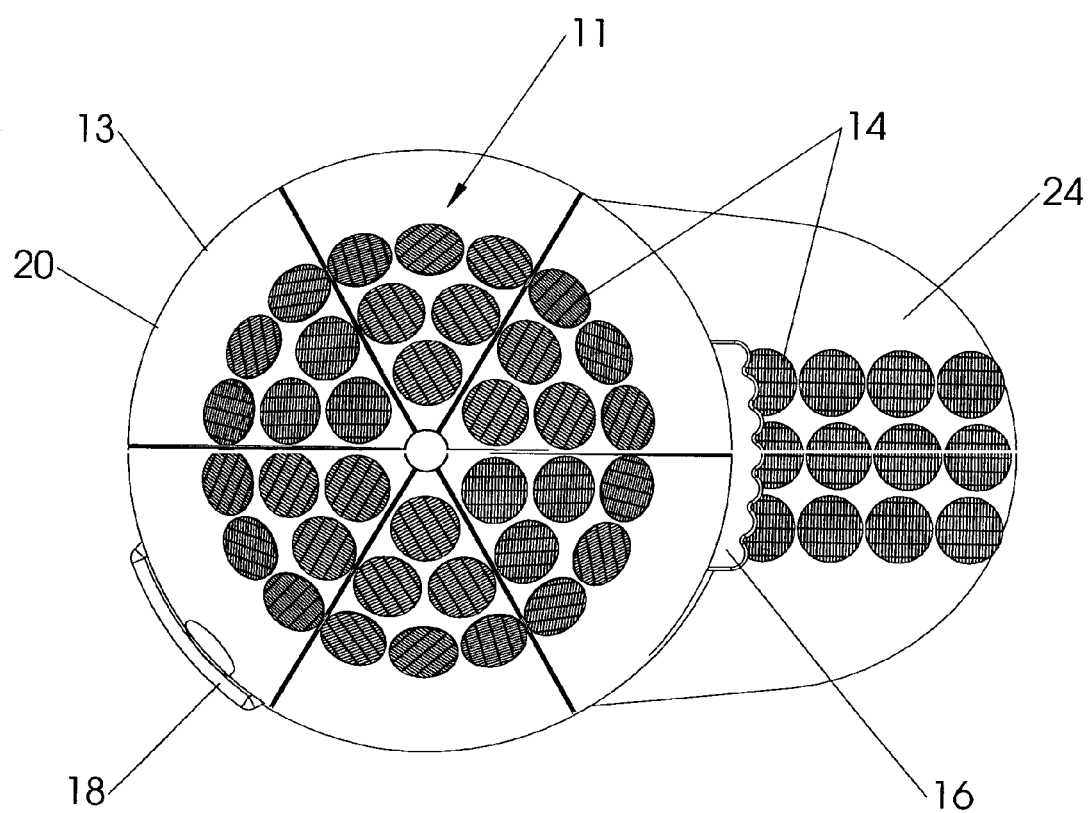
FIG. 1 is a top view of a battery charger.

FIG. 1 is a top view of an example of a battery-charging apparatus 10, wherein the device is based on a conventional baseball cap. A photovoltaic powered inductance charging unit 11 is mounted to the cap 13 for a patient who has an inductance charged, battery-powered device (indicated by reference numeral 30 in FIG. 2) implanted in the skull or brain. Charging unit 11 comprises a plurality of photovoltaic cells 14 mounted on the crown 20 and visor 24 of cap 13, a sending coil 12 (see FIG. 2) mounted at the edge of cap 13, and a charge controller 18 mounted to the cap 13, preferably in proximity to the sending coil 12. The photovoltaic cells 14 allow continuous charging and power for the implanted device when light impinges on them, and cover maximum space on the cap to maximize efficiency, while still maintaining the shape and aesthetics of the baseball cap.

The cap 13 also includes a nonphotovoltaic cell 16, mounted in the front portion of the cap 13, preferably on the junction between the edge of the crown 20 and the visor 24. Nonphotovoltaic cell 16 may be a rechargeable cell, such as model 18650 Li-ion Cell available from Quallion LLC, which is also charged by the photovoltaic cells 14. Nonphotovoltaic cell 16 is used to charge the implanted device in the absence of sufficient power from the photovoltaic cells 14. Alternatively, the nonphotovoltaic cell 16 may be a primary cell, which would need to be replaced periodically to ensure sufficient charge.

Charge controller 18 controls the charging current source and magnitude. That is to say, the charge controller 18 selects either the photovoltaic cells 14, the nonphotovoltaic cell 16, or some other source (described below) as the source of charging current provided to the sending coil 12, and also controls the magnitude of the charging current. The photovoltaic cells 14 are electrically connected to charge controller 18. The nonphotovoltaic cell 16 is also electrically connected to charge controller 18.

Figure 2:
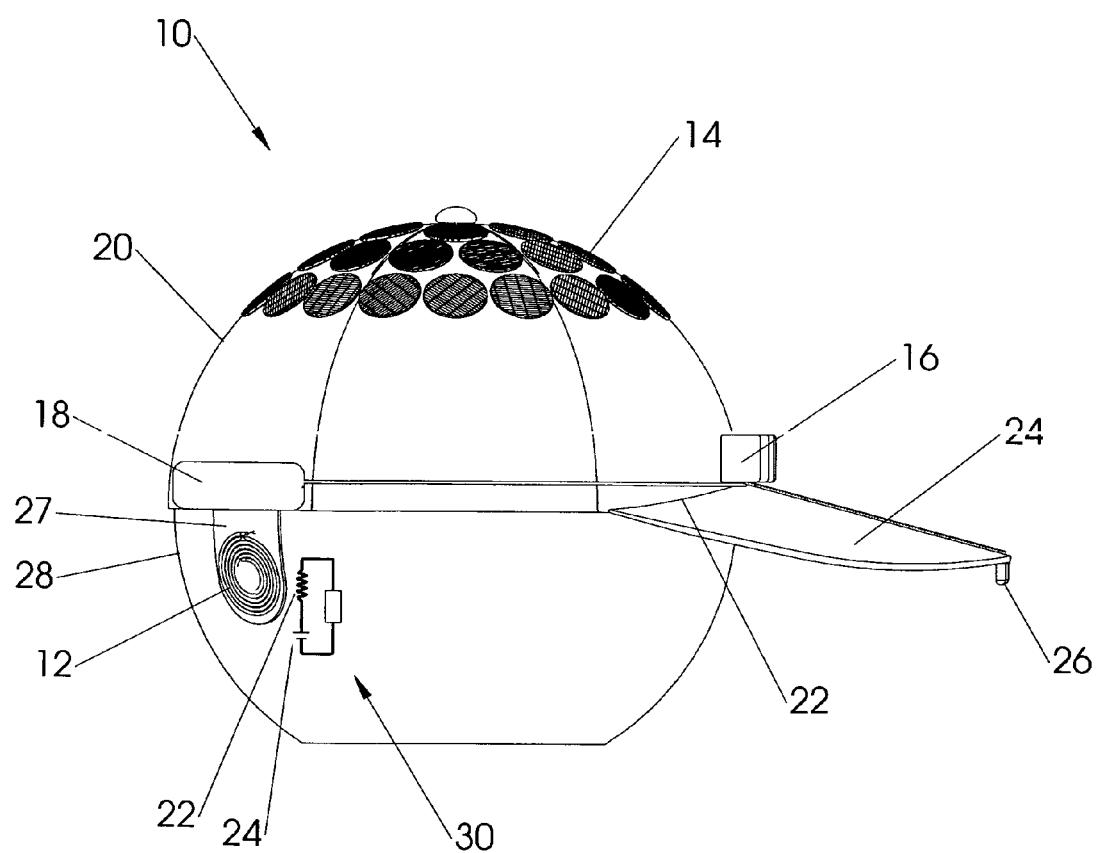
FIG. 2 is a side view of the battery charger of FIG. 1.

As shown in FIG. 2, LED's 26 are mounted on the underside of the visor, remaining just in the peripheral field of normal view, to indicate diagnostic information about the implanted battery. Such information may include whether the battery is in a fully charged state, is being charged, or is completely discharged, which may be indicated by green, yellow, and red, respectively. The LEDs are of a low profile design intended to be easily viewable by the wearer.

The cap 13 has a sending coil 12 mounted on a downwardly-extending tab 27 formed as part of or attached to the hat's band. The tab 27 is located so that when the wearer dons the cap in the conventional manner, the sending coil 12 lines up with the receiving coil 22 for charging the implanted battery 24 of the implanted device 30 in the patient's head 28, or for powering the device, or both. This same pair of coils 12 and 22 may be used for other communication between the charger and the implanted battery, as is known in the art. Alternatively, a second pair of primary and secondary coils (not illustrated) may be provided for communication without having to provide a complex algorithm to accommodate both functions on the same pair of coils.

Figure 3:
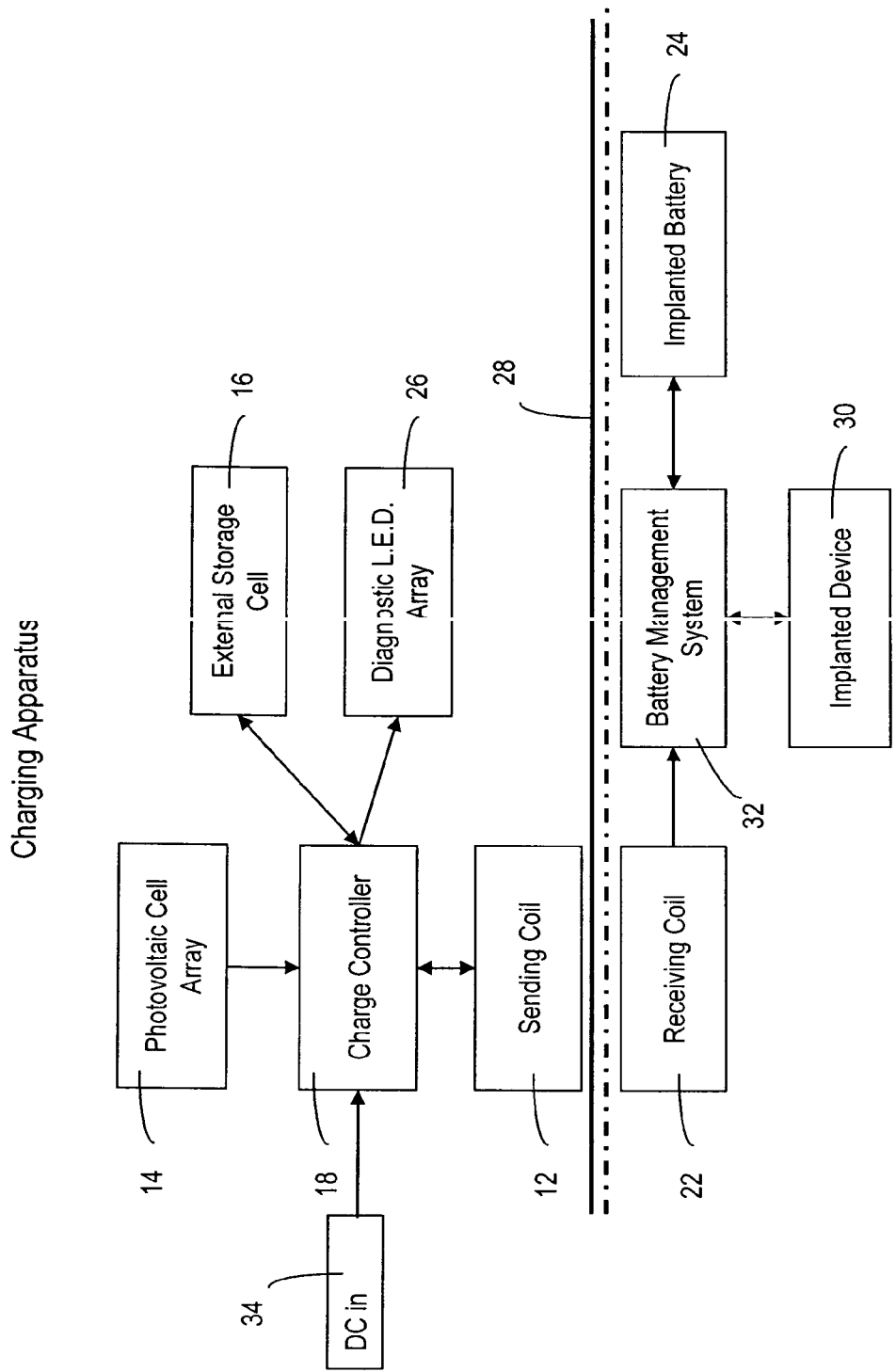
FIG. 3 is a block diagram of a photovoltaic powered charging apparatus for implanted rechargeable batteries in combination with a battery powered implantable device.

A block diagram of a photovoltaic powered charging apparatus for implanted rechargeable batteries in combination with a battery-powered implanted device is shown in FIG. 3. The photovoltaic powered charging apparatus includes elements described above which are mounted to the cap 13. In this regard, the sending coil 12, the photovoltaic cell array 14, the nonphotovoltaic cell 16, and an external power source 34 are electrically connected to the charge controller 18. In the battery-powered implanted device, the receiving coil 22, a battery 24, and circuitry, sensors, and actuators (not shown) of the implanted device 30, are electrically connected to the battery management system 32. Note that the elements 22, 24, 30, and 32 are shown separately. This is for purposes of illustration only as one, some or all of elements 22, 24, and 32 may be integrated into and enclosed in the implantable device 30. In addition, the sending coil 12 is shown aligned with the receiving coil 22 as is desirable to maximize the power coupled or transmitted transcutaneously from the sending to the receiving coil.

As shown in FIG. 3, the battery management system 32, located within the implanted device 30 or within the battery 24 thereof, controls whether the device 30 is powered by the implanted battery or by the inductance coils 12 and 22, based on the level of charge of the battery, the power demand from the device, and the power supplied by the charging coil.

The battery management system 32 and charge controller 18 have the ability to operate cooperatively to direct power to the implanted device 30 by way of the implanted rechargeable battery 24, the nonphotovoltaic cell 16 in the cap, or the photovoltaic cells 14. The charge controller 18 on the cap has the ability to recharge the nonphotovoltaic cell 16 with power obtained from either the external source 34 (AC or DC), or from the photovoltaic cells 14. The battery management system 32 in the implanted device can direct power from the secondary coil 22 to the implanted device 30 while the secondary coil 22 is charging the implanted battery 24. In this way, the battery management system 32 can optimize the charging algorithm and charge state of the implanted battery 24. For example, the battery management system may allow the battery to drain somewhat if it is better for the battery to not remain constantly fully charged. The charge controller and battery management system work together to choose the optimal power source for the implanted medical device and conserve the implanted rechargeable battery.

Figure 4:
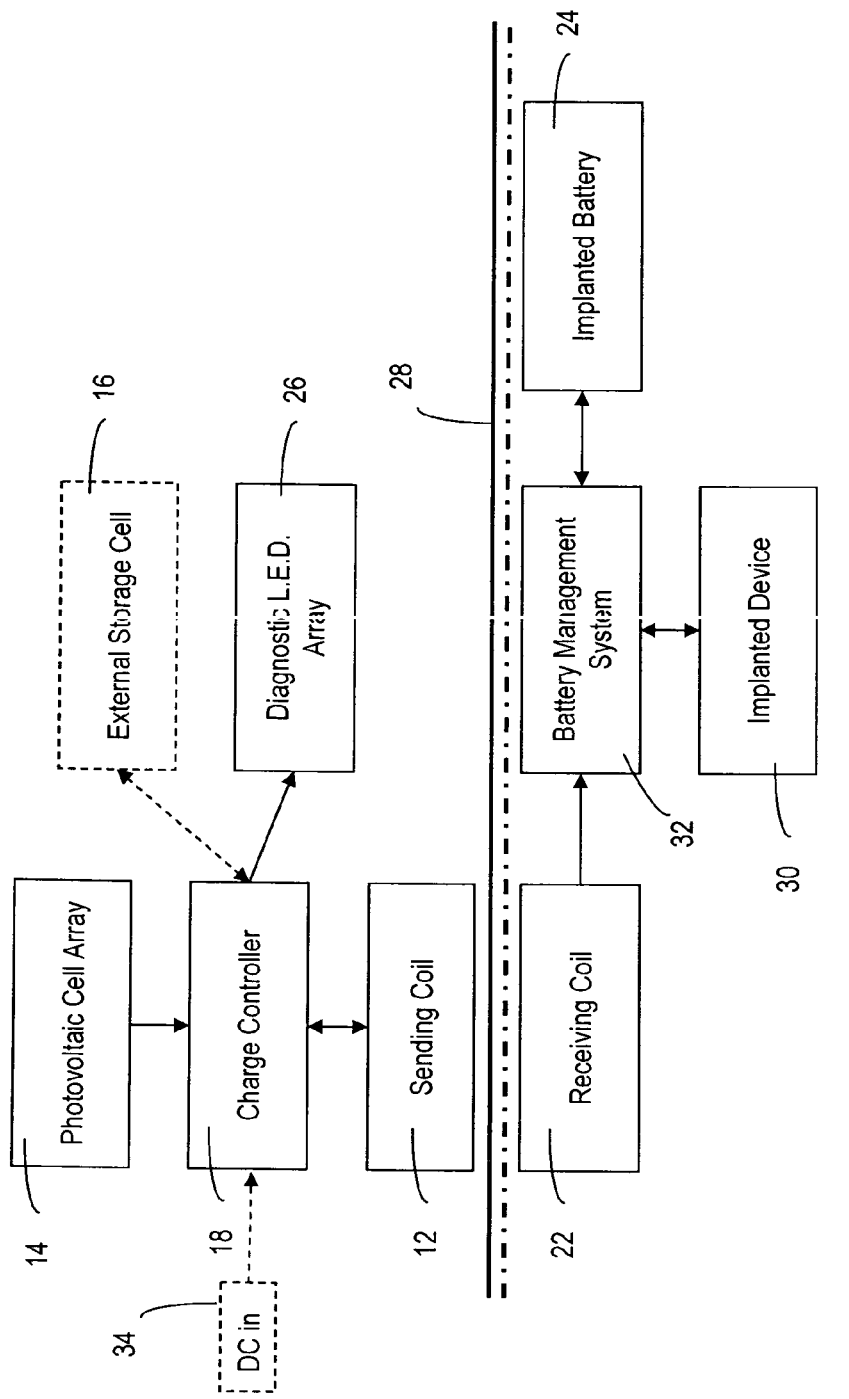
FIGS. 4–11 are block diagrams showing various modes of operation of the apparatus of FIG. 3.
Figure 5:
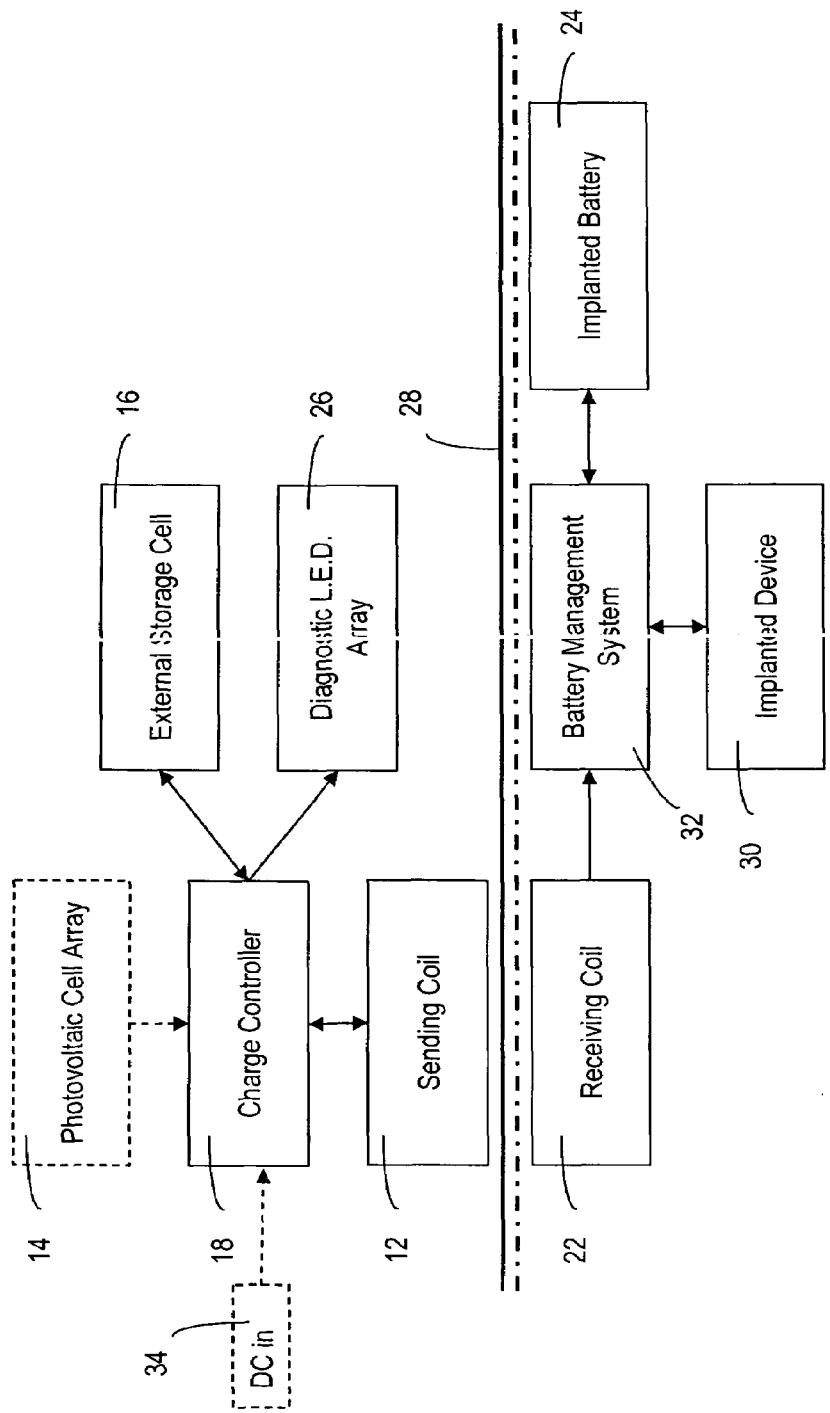
Figure 6:
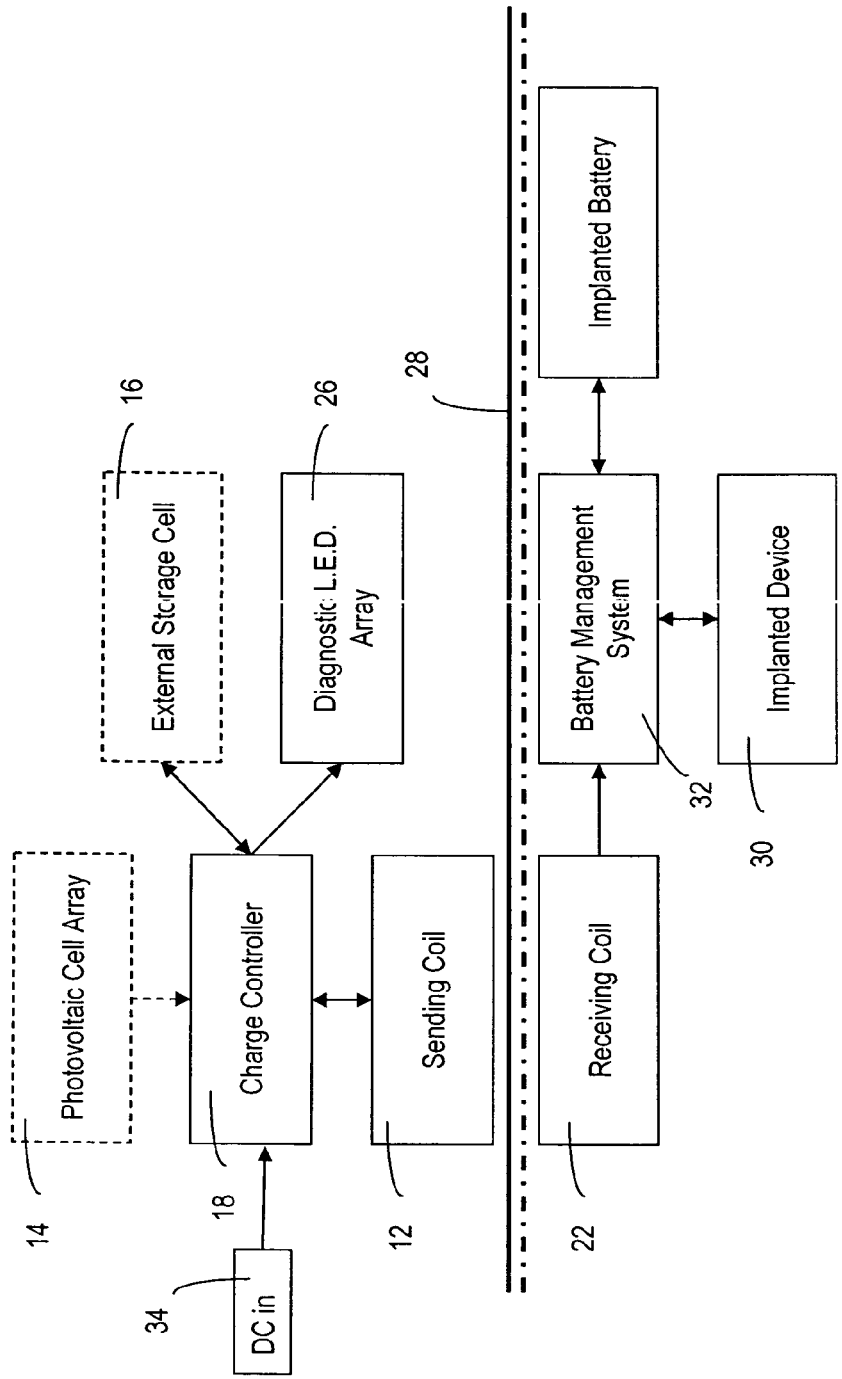
Figure 7:
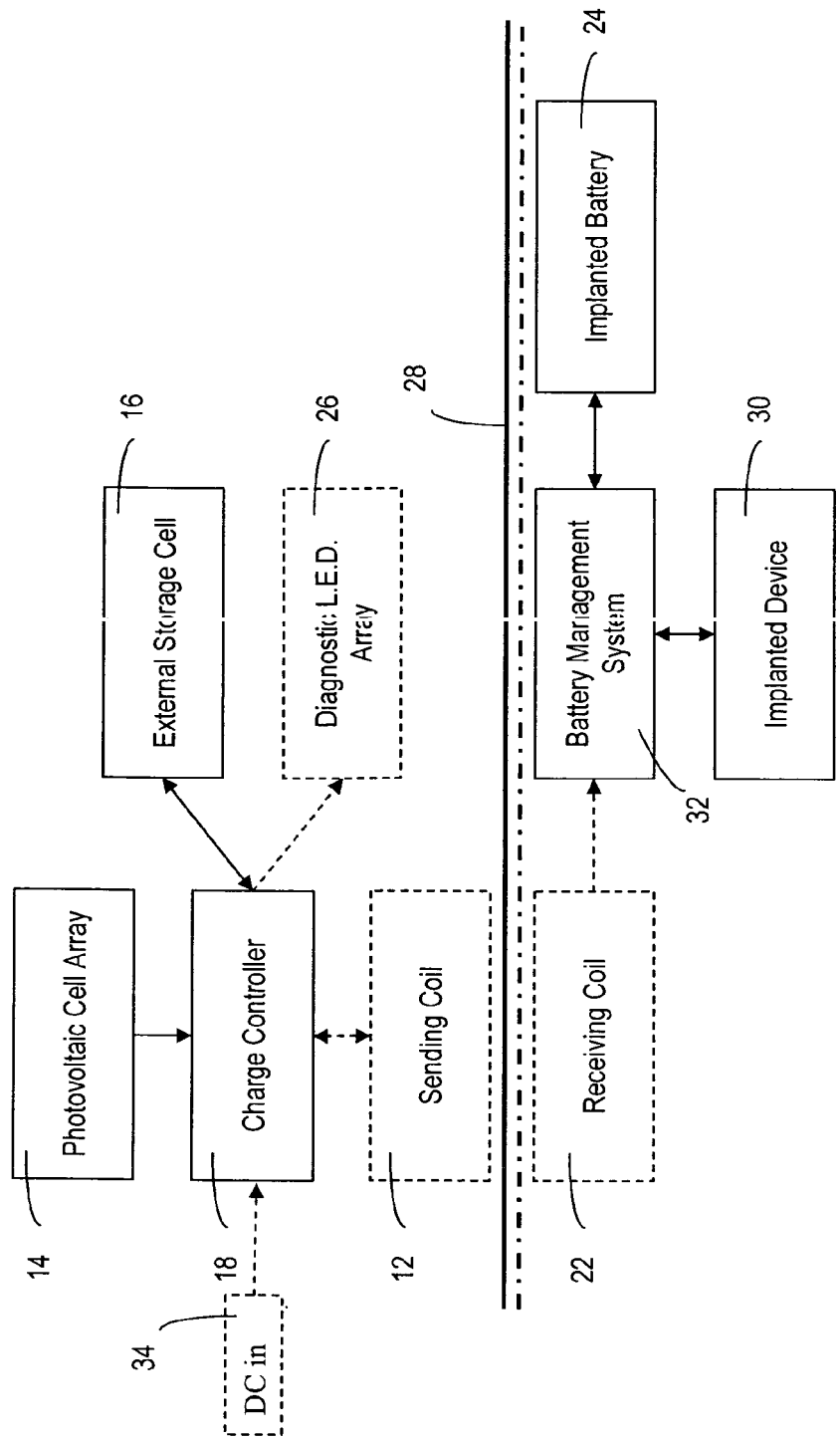
Figure 8:
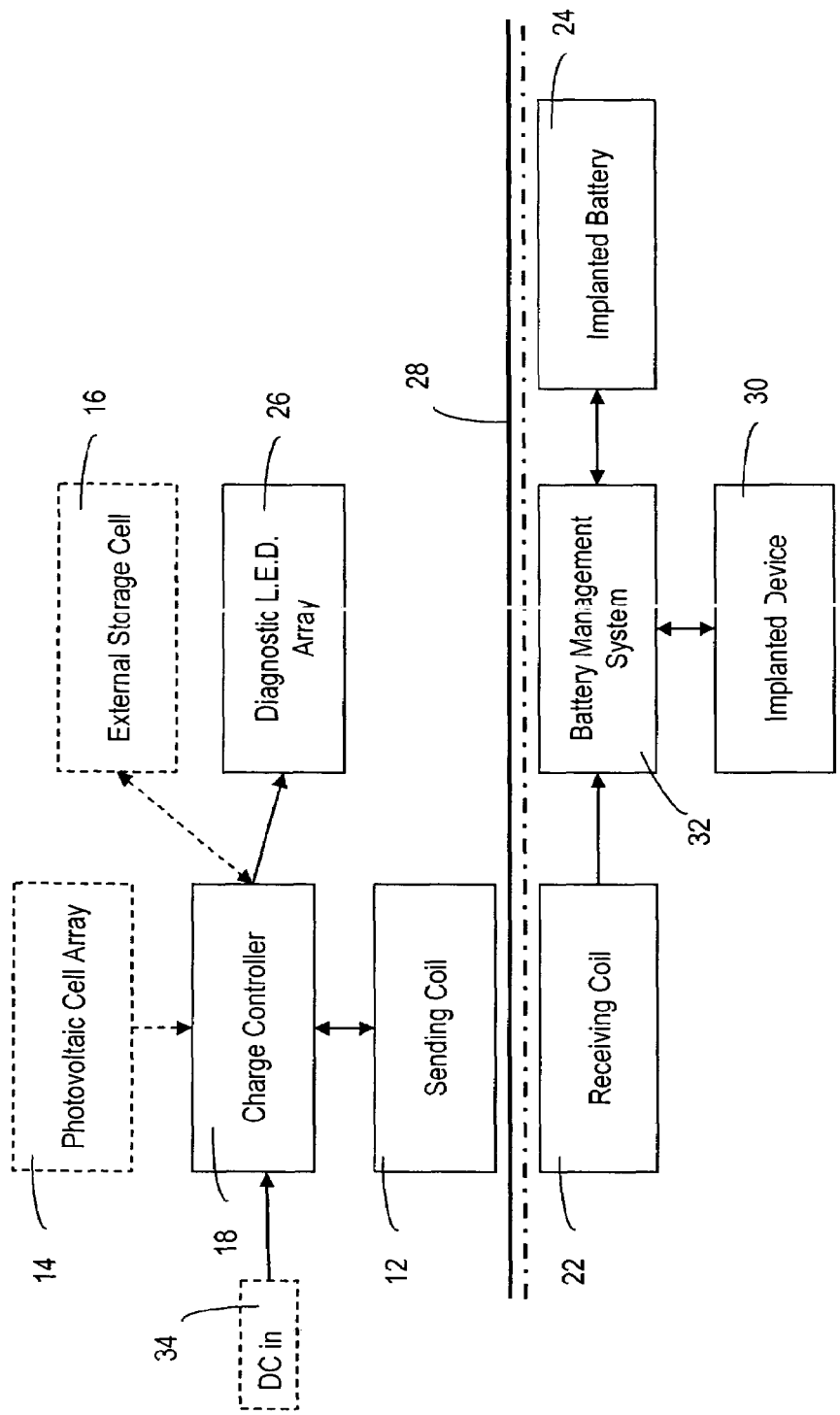
Figure 9:
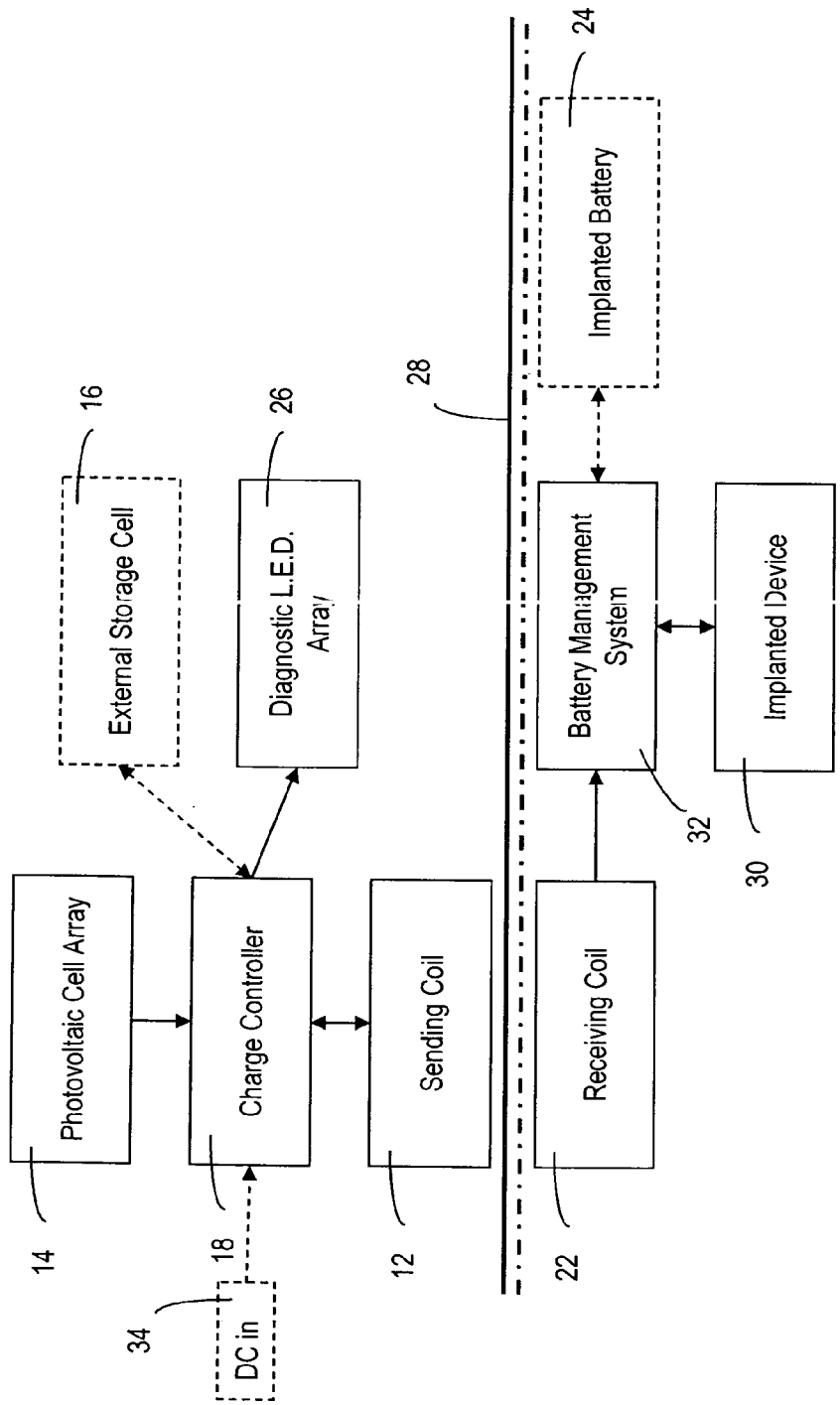
Figure 10:
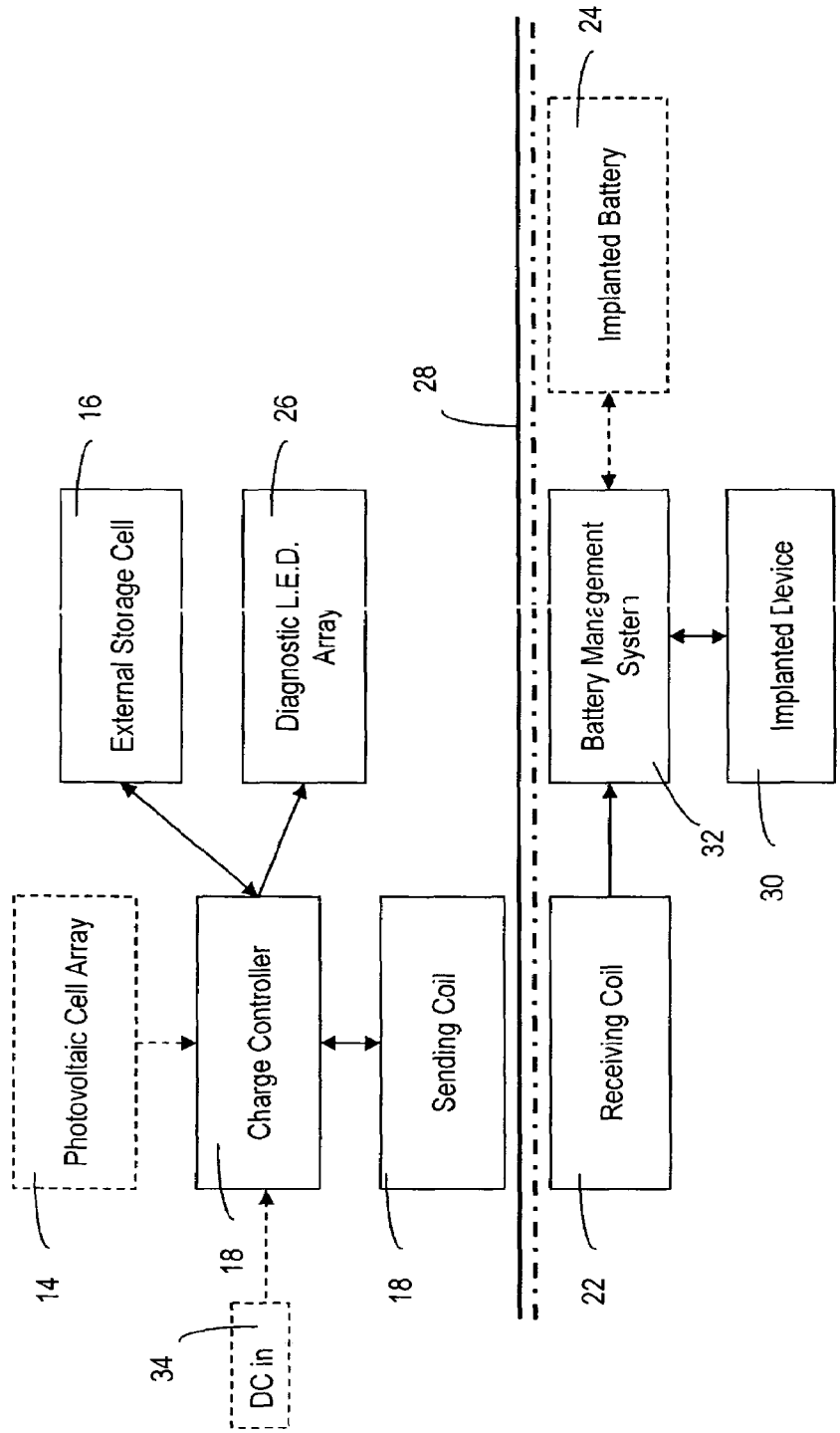
Figure 11:
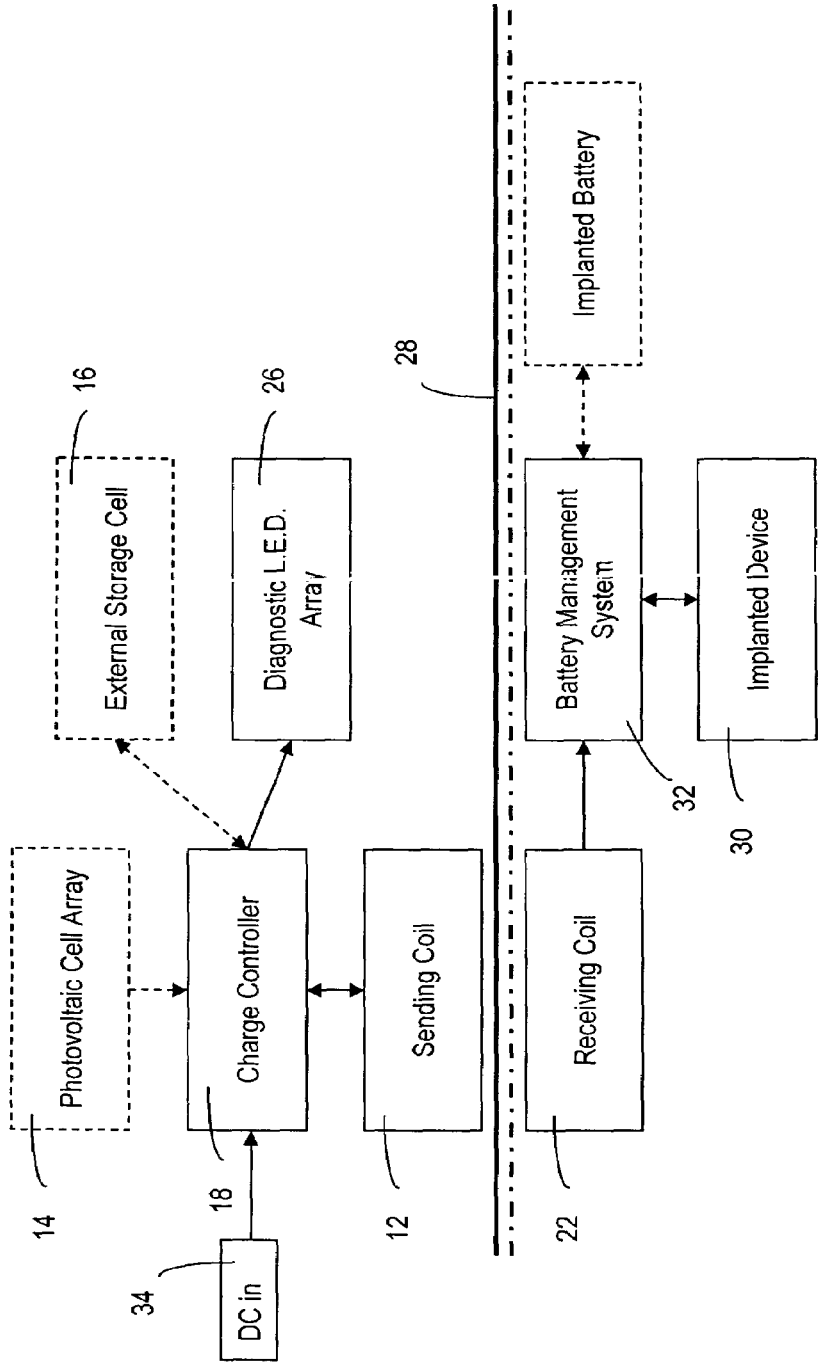

FIGS. 4–11 are block diagrams showing various modes of operation of the rechargeable power source and the battery powered implanted device. In FIG. 4 (Mode 1), the implanted battery 24 is charged from the photovoltaic cell array 14. In FIG. 5 (Mode 2), the implanted battery 24 is charged from the external (nonphotovoltaic) cell 16. In FIG. 6 (Mode 3), the implanted battery 24 is charged from an external DC power source 34. In FIG. 7 (Mode 4), the external (nonphotovoltaic) cell 16 is charged by the photovoltaic cell array 14. In FIG. 8 (Mode 5), the LED array 26 is used to communicate the condition of the implanted battery 24. In FIG. 9 (Mode 6), the implanted device 30 is run from the photovoltaic array 14 via the sending coil 12 and the receiving coil 22. In this mode, neither the external storage cell 16 nor the implanted battery 24 is drained. In FIG. 10 (Mode 7), the implanted device 30 is run from the external (nonphotovoltaic) cell 16. In this mode, the implanted battery 24 is not used to power the device 30. In FIG. 11 (Mode 8), the implanted device 30 is run from an external DC power source 34. In this mode, neither the external storage cell 16 nor the implanted battery 24 is drained, and light is not required because the photovoltaic cell array 14 is not used.

While the invention herein disclosed has been described by means of specific embodiments and applications thereof, numerous modifications and variations could be made thereto by those skilled in the art without departing from the scope of the invention set forth in the claims. Furthermore, various aspects of the invention may be used in other applications than those for which they were specifically described herein. For example, a battery-charging cap may be used to recharge a nonimplanted medical device, such as a hearing aid worn behind the ear; in that case, the recharging may be inductive or direct coupled. Other devices that may be recharged by the cap of the present invention include, but are not limited to, fully implantable speech processor, cochlear implant, deep brain stimulator, and fully implantable middle ossicular stimulator.

What is claimed is:

1. A battery charging apparatus comprising:
    a head covering; and
    a charging unit located on said head covering, said charging unit comprising:
        at least one photovoltaic cell mounted on said head covering;
        a nonphotovoltaic cell mounted on said head covering;
        a sending coil mounted to said head covering for inductively coupling to an implanted secondary coil; and
        a charge controller mounted on said head covering and connected to said at least one photovoltaic cell, said nonphotovoltaic cell, and said sending coil for coupling charging current from said at least one photovoltaic cell or from said nonphotovoltaic cell to said sending coil.

2. The apparatus of claim 1 wherein said nonphotovoltaic cell is a primary cell.

3. The apparatus of claim 1 wherein said nonphotovoltaic cell is a secondary cell.

4. The apparatus of claim 1 wherein said charge controller selects said at least one photovoltaic cell or said nonphotovoltaic cell as a charging source.

5. The apparatus of claim 4 wherein said charge controller is further for controlling the magnitude of a charging current to the sending coil.

6. The apparatus of claim 1 further comprising a battery charge indicator mounted on said head covering.

7. The apparatus of claim 1 wherein said head covering is cap.

8. A rechargeable power source comprising:
    a battery-powered device implanted within the head of a person, a battery connected to said battery-powered device and implanted within the head of said person, and a receiving coil connected to said battery for providing charging current to said battery, said receiving coil implanted in said head of said person; and
    a battery charging apparatus comprising:
        a head covering; and
        a charging unit located on said head covering, said charging unit comprising:
            at least one photovoltaic cell mounted on said head covering; and
            a sending coil mounted to said head covering for being aligned with said receiving coil, said sending coil electrically coupled to said at least one photovoltaic cell for inductively coupling power collected by said at least one photovoltaic cell to said receiving coil.

9. The power source of claim 8 wherein said charging unit further comprises a nonphotovoltaic cell electrically coupled to said sending coil and mounted on said head covering.

10. The apparatus of claim 9 wherein said nonphotovoltaic cell is a primary cell.

11. The apparatus of claim 9 wherein said nonphotovoltaic cell is a secondary cell.

12. The apparatus of claim 9 further comprising a charge controller on said head covering and connected to said at least one photovoltaic cell and to said nonphotovoltaic cell.

13. The apparatus of claim 12 wherein said charge controller selects either said at least one photovoltaic cell or said nonphotovoltaic cell as a charging source.

14. The apparatus of claim 13 wherein said charge controller controls a magnitude of a charge current to said receiving coil.

15. The apparatus of claim 14 further comprising a battery charge indicator mounted on said head covering.

16. The apparatus of claim 14 wherein said head covering is cap.

17. The apparatus of claim 9 further comprising a battery management system implanted in said person for controlling whether the device is powered by said implanted battery or by said sending coil.

18. The apparatus of claim 12 further comprising a battery management system implanted in said person for controlling whether the device is powered by said implanted battery or by said sending coil.

19. A method for recharging an implanted battery using a head covering having a charging unit located thereon, said charging unit comprising:
    a plurality of photovoltaic cells mounted on said head covering; and
    a sending coil mounted to said head covering for inductively coupling to an implanted receiving coil, said sending coil electrically coupled to said plurality of photovoltaic cells;
    the method comprising the steps of:
        disposing the head covering to align the sending coil with a location of the implanted receiving coil;
        exposing the head covering to light;
        coupling power generated by the plurality of photovoltaic cells from the sending coil to the receiving coil; and
        coupling current for recharging the implanted battery from the receiving coil to the implanted battery.

20. The method of claim 19, wherein the charging unit further includes a nonphotovoltaic cell disposed on the head covering, the method further including the steps of selecting the plurality of photovoltaic cells or the nonphotovoltaic cell as a source of charging power, and coupling power from the source of charging power to the sending coil.

21. The method of claim 20, wherein the charging unit further includes a source of external power and the step of selecting includes selecting the plurality of photovoltaic cells, the nonphotovoltaic cell, or the source of external power as a source of charging power.

22. A combination for providing power to an implanted device, comprising
    a head cover;
    a sending coil mounted to said head cover for alignment with an implanted receiving coil;
    a plurality of photovoltaic cells on said head cover;
    a nonphotovoltaic cell on said head cover;
    means for receiving power from a source off of said head cover; and
    a charge controller on said head cover and connected to said sending coil, said plurality of photovoltaic cells, said nonphotovoltaic cell, and said means to select one of said plurality of photovoltaic cells, said nonphotovoltaic cell, or said means to provide a charging current for the sending coil.

23. A combination for providing power through skin, comprising
    an implantable device with a receiving coil, a rechargeable battery, and a power management system connected to said receiving coil and said battery for selecting said receiving coil or said battery for providing to said implantable device and for coupling a charging current from said receiving coil to said battery; and a charging unit with a head cover, a sending coil mounted to said head cover for alignment with said receiving coil, a plurality of photovoltaic cells on said head cover, a nonphotovoltaic cell on said head cover, means for receiving power from a source off of said head cover, and a charge controller on said head cover and connected to said sending coil, said plurality of photovoltaic cells, said nonphotovoltaic cell, and said means to select one of said plurality of photovoltaic cells, said nonphotovoltaic cell, or said means to provide a charging current for said sending coil.

* * * * *